United States Patent [19]

Dingerdissen et al.

[11] Patent Number: 4,694,069

[45] Date of Patent: Sep. 15, 1987

[54] KIBDELOSPORANGIUM ARIDUM SK&F-AAD-609

[75] Inventors: John J. Dingerdissen, West Chester; Rajanikant Mehta, King of Prussia; Louis J. Nisbet, Rosemont; Marcia C. Shearer, Conshohocken; Gail F. Wasserman, Devon, all of Pa.

[73] Assignee: SmithKline Beckman Corporation, Philadelphia, Pa.

[21] Appl. No.: 781,422

[22] Filed: Sep. 30, 1985

[51] Int. Cl.$^4$ .................. A61K 35/74; C12P 1/00; C12P 1/04

[52] U.S. Cl. .................. 530/317; 530/321; 530/322; 424/118; 435/169; 426/635; 426/636

[58] Field of Search .................. 530/317, 321, 322; 424/118; 435/169; 210/656; 426/635, 636

[56] References Cited

U.S. PATENT DOCUMENTS 4,521,335 6/1985 Chan-Sitrin .
4,548,974 10/1985 Bowie et al. .................. 436/169

Primary Examiner—John Kight
Assistant Examiner—Nathan M. Nutter
Attorney, Agent, or Firm—Edward T. Lentz; Janice E. Williams; Alan D. Lourie

[57] ABSTRACT

A novel subspecies of *Kibdelosporangium aridum*, subsp. *largum* (SK&F-AAD-609) produces AAD-216 antibiotics and AAD-609 antibiotics, the ADD-609 antibiotics differing from the AAD-216 antibiotics in presence of glucosamine in the glycolipid radical in place of amino glucuronic acid.

40 Claims, No Drawings

KIBDELOSPORANGIUM ARIDUM SK&F-AAD-609

FIELD OF THE INVENTION

This invention relates to a strain of *Kibdelosporangium aridum* which produces glycopeptide antibiotics.

BACKGROUND OF THE INVENTION

*Kibdelosporangium aridum* Shearer gen. nov., sp. nov. SK&F-AAD-216 is disclosed in U.S. patent application Ser. No. 513,513 and was U.S. Pat. No. 4,548,974. A complex of glycopeptide antibiotic compounds designated AAD-216 and, specifically, three major components of the complex, AAD-216A, AAD-216B and AAD-216C are also disclosed therein. The AAD-216 aglycone, the common pseudoaglycone and the major factor aglycones of AAD-216 are disclosed in U.S. Pat. No. 4,521,335. U.S. patent application Ser. No. 513,513, allowed May 14, 1985, and U.S. Pat. No. 4,521,335, issued June 4, 1985, are incorporated by reference herein as though fully set forth.

SUMMARY OF THE INVENTION

In one aspect, this invention is a novel subspecies of *Kibdelosporangium aridum*, namely, subspecies *largum*, designated SK&F-AAD-609. This subspecies has the identifying characteristics of ATCC 39922.

In another aspect, this invention is novel glycopeptide antibiotics which are structurally and biologically related to the AAD-216 antibiotics. In this aspect, the invention is a variant AAD-216 antibiotic which differs from the AAD-216 antibiotic in that the sugar moiety within the glycolipid radical is glucosamine rather than aminoglucuronic acid. More particularly, therefore, the invention is a compound of the formula (I):

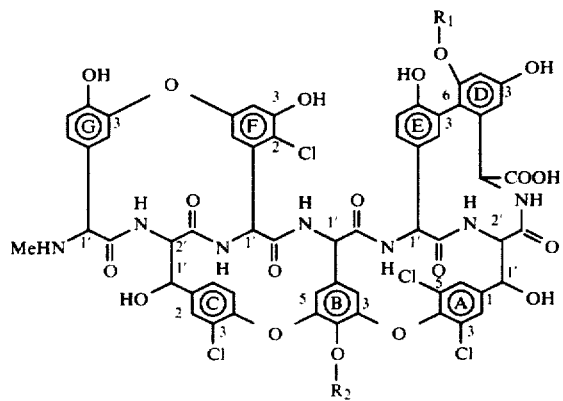

wherein $R_1$ is mannosyl or —H and $R_2$ is

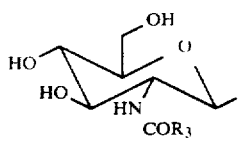

wherein $R_3$ is $C_{8-12}$ alkyl or alkenyl, branched or linear, optionally substituted by hydroxyl, and the desoxy analogs thereof.

DETAILED DESCRIPTION OF THE INVENTION

*Kibdelosporangium aridum* subsp. *largum* (SK&F-AAD-609) produces AAD-216 antibiotics as well as variants thereof, herein referred to as the AAD-609 antibiotics. Strain SK&F-AAD-609 was isolated from a desert soil collected in Pima County, Arizona.

Stock cultures of SK&F-AAD.-609 were maintained on thin potato-carrot agar or oatmeal agar. Morphological observations were made on plates of thin potato-carrot agar, oatmeal agar, water agar or soil extract agar. Inoculum for the physiological and biochemical tests was prepared by adding the contents of a frozen vial to a flask of glucose-yeast extract broth which was placed on a rotary shaker at 28° C., 250 RPM for three to five days. The culture was harvested by centrifugation and washed three times with sterile distilled water. Incubation temperature for the biochemical and physiological tests was 28° C. Readings of the results were made at various times up to 21 days for the plate media. Most of the tubed media were read at various times up to 28 days. However, the tests for decomposition of urea, allantoin and hippurate, as well as the tests for reduction of nitrates, were read for six weeks.

Susceptibility of SK&F-AAD-609 to antibiotics was examined by placing BBL susceptibility disks on nutrient agar plates seeded with SK&F-ADD-609 as an agar overlay. Plates were placed at 4° C. for one hour to permit diffusion of the the anitbiotics and, subsequently, incubated at 28° C. Diameters of the zones of inhibition were measured after incubation for one week.

Morphology. Strain SK&F-ADD-609 is a filamnetous organism that forms a mycelium differentiated into: (1) a substrate mycelium that penetrates the agar and forms a compact layer on top of the agar, and (2) an aerial mycelium that bears chains of conidia and/or sporangium-like structures. No motile elements were observed in either the aerial or substrate mycelium.

Substrate Mycelium. SK&F-AAD-609 produces a well developed substrate mycelium which may undergo fragmentation without displacement. The long, moderately branching hyphae are septate and about 0.5 μm–1.0 μm in diameter. Present on the substrate hyphae are specialized structures which consist of dichotomously branched, septate hyphae radiating from a common stalk. These specialized structures are produced either deep in the agar or just below the surface of the agar and appear to be "naked" sporangium-like structures analogous to the conidial structures which Couch (Couch, J. N., J. Elisha Mitchell Scient. Soc. 79, 53–70, 1963) described on the substrate hyphae of the Actinoplanaceae. On many media SK&F-AAD-609 produces characteristic crystals in the agar.

Aerial Mycelium. The aerial mycelium of SK&F-AAD-609 produces straight or irregularly curved chains of rod-shaped, smooth-walled spores which are irregular in length (0.5 μm×0.8–3.2 μm). These spore chains are usually very long with more than 50 spores per chain, but a few short chains of ten spores or less are also usually present. The spore chains are born apically on the main thread or on lateral branches. When placed on agar these spores germinate with the production of one or more germ tubes.

On most media, the aerial mycelium of SK&F-AAD-609 also produces sporangium-like structures. These are born apically on branched or unbranched hyphae; they are also born terminally on lateral branches of the main hyphal thread. Sporangium-like structures and chains of spores are frequently born on the same aerial hypha. Mature sporangium-like structures are usually round, approximately 12 μm–μ32 m in diameter. Sporangium-like structures slightly flattened in one axis or very irregularly shaped are also observed. These sporangium-like structures are surrounded by a well-defined wall and, at maturity, contain septate, branched hyphae embedded in an amorphous matrix. When placed on agar, these sporangium-like structures germinate directly with the production of one or more germ tubes.

Chemotaxonomy. Purified cell wall preparations of SK&F-AAD-609, analyzed by the method of Becker (Becker, B. et al., Appl. Microbiol. 13:236–43, 1965) contained the meso-isomer of 2,6-diaminopimelic acid, alanine, glutamic acid, glucosamine, muramic acid, galactose and a very minor amount of arabinose. Whole-cell hydrolysates analyzed by the method of Lechevalier (Lechevalier, M. P., J. Lab. Clin. Med. 71:934–44, 1968) contained galactose, glucose, mannose, ribose, rhamnose, a major amount of arabinose and a trace of madurose. No mycolic acids of any type were present in the cell extracts analyzed for lipid patterns by the method of Lechevalier (Lechavalier, M. P., et al., Can. J. Microbiol. 19:965–72, 1973). The phospholipids present were phosphatidyl ethanolamine, phosphatidyl innositol mannosides, phosphatidyl innositol and diphosphatidyl glycerol. Thus, SK&F-AAD-609 has a Type IV cell wall with a unique whole-cell sugar pattern, Type A plus a trace of madurose (Lechevalier, M. P., et al., Int. J. Syst. Bacteriol. 20:435–43, 1970) and a phospholipid pattern of type PII (Lechevalier, M. P., et al., Biochem System. Ecol. 5:249–60, 1977).

Biochemical and Physiological Characteristics. SK&F-AAD-609 is gram positive and not acid-fast. No growth takes place under anaerobic conditions. Temperature range for growth is 15° C. to 42° C. with a trace of growth at 45° C.; growth at 10° C. is inconsistent. No growth occurs at 50° C. Hydrogen sulfide is produced. Milk is peptonized. Gelatin is both hydrolyzed and liquified. Nitrate reduction to nitrite is doubtful. Melanin pigments are produced. Casein, L-tyrosine, hypoxanthine, guanine and elastin are hydrolyzed but starch, adenine, xanthine and cellulose (Avicel) are not. Phosphatase and catalase are produced. Urea, esculin and hippurate are decomposed; tests for allantoin decomposition are weakly positive. SK&F-AAD-609 grows on 2% NaCl. There is no growth in 8% NaCl; growth in 3–7% NaCl is inconsistent. No growth occurs in lysozyme broth. Acid is produced from L-arabinose, D-cellobiose, dextrin, dextrose, D-fructose, glycerol, glycogen, D-galactose, i-inositol, lactose, D-mannitol, D-mannose, maltose, α-methyl-D-glucoside, α-methyl-D-mannoside, melibiose, D-melezitose, raffinose, rhamnose, D-ribose, sucrose, trehalose and D-xylose. No acid is produced from dulcitol, i-erythritol, inulin or L-sorbose. Citrate, malate, succinate, oxalate, lactate, acetate, pyruvate, formate and propionate are utilized; benzoate and tartrate are not.

Susceptibility to Antibiotics. By the diffusion method, SK&F-AAD-609 was resistant to disks impregnated with gentamicin (10 µg), tobramycin (10 µg), ampicillin (10 µg), penicillin (10 units), lincomycin (2 µg), streptomycin (10 µg), vancomycin (30 µg), clindamycin (2 µg), chloramphenicol (5 µg) and cephalothin (30 µg). Chlortetracycline (5 µg) produced 17–18 mm zones of inhibition; tetracycline (5 µg) 9–12 mm zones; rifampin (5 µg) 10–12 mm zones; novobiocin (5 µg) 30–35 mm zones. All zones of inhibition contained at least a few resistant colonies.

Description of SK&F-AAD-609 on Various Media. All cultures were incubated at 28° C. in closed petri dish cans and observed at intervals up to 21 days. The colors of the culture were chosen following comparison with color chips from either the ISCC-NBS Centroid Color Charts or the Dictionary of Color (Maerz, A., and M. R. Paul, 2nd. ed. New York: McGraw Hill Book Co., Inc. 1950).

Yeast Extract-Malt Extract Agar. Growth good to excellent; vegetative mycelium yellow-brown; aerial mycelium none visible to very sparse, white; spore chains and sporangium-like structures, sparse; yellow-brown soluble pigment; characteristic crystals present in agar.

Oatmeal Agar. Growth fair to good; vegetative mycelium off-white to pale yellow-brown; aerial mycelium moderate, white; spore chains and sporangium-like structures present; pale yellow-brown soluble pigment variably present; characteristic crystals present in agar.

Glycerol-Asparagine Agar. Growth fair to good; vegetative mycelium off-white to pale yellow-brown; aerial mycelium none to sparse, white; spore chains and sporangium-like structures, none to abundant; pale yellow-brown soluble pigment; characteristic crystals present in agar.

Inorganic Salts-Starch Agar. Growth fair to good; vegetative mycelium off-white to pale yellow-brown; aerial mycelium none visible to sparse, white; spore chains and sporangium-like structures present; pale yellow-brown soluble pigment variably present; characteristic crystals present in agar.

Czapek-Sucrose Agar. Growth good; vegetative mycelium off-white to pale yellow-brown; aerial mycelium moderate to abundant, white; spore chains and sporangium-like structures present; pale yellow-brown soluble pigment; characteristic crystals present in agar.

Bennett's Agar. Growth fair to good; vegetative mycelium off-white to grayish yellow-brown; aerial mycelium none to sparse, white; spore chains and sporangium-like structures, none to moderate; grayish yellow-brown soluble pigment; characteristic crystals variably present in agar.

Nutrient Agar. Growth fair; vegetative mycelium grayish yellow-brown; aerial mycelium sparse, white, sterile; no spore chains or sporangium-like structures observed; yellow-brown soluble pigment; no crystals detected in agar.

Thin Potato-Carrot Agar. Growth fair; vegetative mycelium off-white to pale yellow-brown; aerial mycelium sparse to moderate, white to light gray; numerous spore chains and sporangium-like structures present; pale yellow-brown soluble pigment variably present; characteristic crystals variably present in agar.

Starch-Casein Nitrate Agar. Growth good; vegetative mycelium off-white to pale yellow-brown; aerial mycelium none to sparse, white; spore chains and sporangium-like structures present; pale yellow-brown soluble pigment variably present; characteristic crystals present in agar.

Water Agar. Growth poor; vegetative mycelium translucent to off-white, aerial mycelium sparse to moderate, white to light gray; spore chains and sporangium-like structures present; no soluble pigment; no crystals detected in agar.

Yeast Extract-Glucose Agar. Growth fair to good; vegetative mycelium grayish yellow-brown; aerial mycelium, none visible; under 400× a few spore chains but no sporangium-like structures present; yellow-brown soluble pigment; characteristic crystals variably present in agar.

Soil Extract Agar. Growth fair; vegetative mycelium off-white to pale yellow-brown; aerial mycelium sparse to moderate, white to light gray; spore chains and sporangium-like structures present; no soluble pigment; no crystals detected in agar.

Peptone-Yeast Extract-Iron Agar. Growth good; vegetative mycelium grayish brown (Maerz & Paul 16H8); no aerial mycelium visible; no spore chains or sporangium-like structures present; soluble pigment brownish-black; no crystals detected in agar.

A comparison of the description of SK&F-AAD-609 with the description of actinomycetes listed in Bergey's Manual of Determinative Bacteriology, The Approved List of Bacterial Names and other recent taxonomic literature indicates that SK&F-AAD-609 does not belong to the genera described therein. Strain SK&F-AAD-609 belongs to the genus *Kibdelosporangium*, first described in U.S. patent application Ser. No. 513,513. It was compared directly with the one species previously placed in this genus, *K. aridum*. Strain SK&F-AAD-609 differs from *K. aridum* in several minor morphological and chemotaxonomic characteristics, as well as antibiotic production. Some of the differences noted between SK&F-AAD-609 and *K. aridum* may be attributed to vigor, i.e., the aerial mycelium of SK&F-AAD-609 is denser and the sporangium-like structures are usually larger than those of *K. aridum*. When grown in the dark, SK&F-AAD-609 frequently produces a pale gray aerial mycelium on thin potato-carrot agar, water agar and soil extract agar. This was never observed in *K. aridum* and the aerial mycelium of both cultures is white when grown in the light. The phospholipid pattern of the two organisms also differs slightly; phosphatidyl methylethanolamine is present in *K. aridum* but was not detected in SK&F-AAD-609. Strain SK&F-AAD-609 produces the major components of the antibiotic complex produced by *K. aridum*, AAD-216-A, AAD-216-B, AAD-216-C and AAD-216-C$_2$. In addition, SK&F-AAD-609 produces the N-acetylglucosamine analogs of these compounds which were not found in fermentation broths from *K. aridum*.

The differences between SK&F-AAD-609 and *K. aridum* are judged insufficient to warrant the erection of a new species. Strain SK&F-AAD-609 is, therefore, designated a new subspecies of *K. aridum* for which we propose the name, *Kibdelosporangium aridum* subsp. *largum* subsp. nov. (largus, L. adj., abundant, plentiful, numerous). *K. aridum* subsp. *largum* (SK&F-AAD-609) has been deposited in the American Type Culture Collection, Rockville, Md. under the accession number ATCC 39922.

The novel AAD-609 antibiotics produced by *K. aridum* AAD-609 are identical to the AAD-216 antibiotics except that in place of aminoglucuronic acid in the glycolipid moiety of the AAD-216 antibiotics, the AAD-609 antibiotics have glucosamine. More particularly, the AAD-609 antibiotics have the formula (I), shown above.

The AAD-216 complex and factors A, B and C are disclosed in U.S. patent application Ser. No. 513,513. In addition to the major components, Factors A, B and C, approximately thirty-five other antibiotic factors have been identified within the AAD-216 complex. All the AAD-216 factors share in common the core aglycone shown in formula (I), above, or the desoxy analog thereof lacking the benzylic hydroxyl in Ring C. In all AAD-216 factors identified to date, $R_3$ is a $C_{8-12}$ alkyl or alkenyl, branched or linear, optionally substituted by a hydroxyl.

In Factor A, $R_3$ is $-(CH_2)_8CH_3$.
In Factor B, $R_3$ is $-(CH_2)_7CH(CH_3)_2$.
In Factor C, $R_3$ is $-(CH_2)_8CH(CH_3)_2$.

Though not isolated from the AAD-609 complex, it appears that the AAD-609 complex commprises factors analogous to all of the AAD-216 factors, differing only in that in the AAD-609 factors, $R_2$ is glucosamine whereas in AAD-216 factors, $R_2$ is aminoglucuronic acid. Therefore, in the AAD-609 antibiotics, $R_3$ is the same as in the AAD-216 antibiotics.

The following table lists certain characteristics of the AAD-216 factors other than A, B and C. The characteristics shown are the HPLC retention times, the gas chromatography retention time (GC-RT) of methyl esters of the fatty acid ($R_3CO_2CH_3$) and the molecular weights by GC mass spectroscopy of the methyl esters. $R_3$ in the AAD-609 factors, by inference, has the same characteristics.

| AAD-216 Factor | HPLC RT | GC-RT | MW |
|---|---|---|---|
| F1 | 5.9 | 11.8 | 216 |
| 2 |  | 11.9 | 214 |
| 3 |  | 12.1 | 216 |
| G1 | 7.7 | 10.8 | 212 |
| 2 |  | 12.9 | 230 |
| 3 |  | 13.0 | 230 |
| H | 8.4 | 13.8 | 230 |
| J | 8.7 | 13.3 | 230 |
| K | 9.1 | 13.8 | 230 |
| L1 | 9.2 | 13.3 | 230 |
| 2 |  | 13.6 | 230 |
| 3 |  | 13.8 | 228 |
| M1 | 10.1 | 14.1 | 244 |
| 2 |  | 14.1 | 244 |
| 3 |  | 13.3 | 230 |
| N |  | 10.6 | 14.1 | 244 |
| O |  | 10.7 | 14.6 | 244 |
| P1 | 11.4 | 14.5 | 244 |
| 2 |  | 9.7 | 202 |
| 3 |  | 6.5 | 172 |
| Q | 11.7 | 9.7 | 202 |
| D | 12.8 | 7.9 | 184 |
| R | 13.6 | 8.2 | 184 |
| S | 14.0 | 7.4 | 186 |
| B1 | 16.3 | 7.9 | 186 |
| B2 | 16.7 | 8.9 | 200 |
| B3 | 17.8 | 9.3 | (1) |
| B3-4 | 17.9 | 9.3 | (1) |
|  |  | 10.0 | (1) |
|  |  | 10.5 | (1) |
| B5 | 18.8 | 8.7 | (1) |
| C1 | 19.6 | 10.2 | 214 |
| C2 | 20.1 | 10.6 | 214 |
| C3 | 20.7 | 10.0 | 214 |
| C4 | 20.8 | 10.6 | 214 |
| C5 | 21.0 | 11.4 | 226 |
| C5-6 | 21.3 | 11.3 | 226 |
|  |  | 11.4 | 226 |

(1) GC Mass spectroscopy not done. Based on GC-RT, the molecular weight is presumed to be 200.

Absolute GC retention times, of course, will vary with conditions of a given run. In the same GC assay, a commercially available standard mix of methyl esters of $C_{8-12}$ fatty acids (Supelco) had the following GC retention times:

| | |
|---|---|
| $C_7H_{15}CO_2CH_3$ | 5.2 |
| $C_8H_{17}CO_2CH_3$ | 6.6 |
| $C_9H_{19}CO_2CH_3$ | 7.9 |
| $C_{10}H_{21}CO_2CH_3$ | 9.3 |
| $C_{11}H_{23}CO_2CH_3$ | 10.6 |

The following table shows the predicted structure (number of carbon atoms, presence of hydroxyl (if any), unsaturation (if any) and branching of the chain (if any)) of the fatty acid ($R_3COOH$) of each of the above AAD-216 factors.

| AAD-216 Factor | Formula ($R_1COOH$) |
|---|---|
| F1 | $C_{11}$,OH |
| 2 | $C_{11}$,OH, olefin |
| 3 | $C_{11}$OH |
| G1 | $C_{12}$, olefin |
| 2 | $C_{12}$,OH |
| 3 | $C_{12}$,OH |
| H,J,K,L1,L2 | $C_{12}$,OH |
| L3 | $C_{12}$,OH, olefin |
| M1,2 | $C_{13}$,OH |
| 3 | $C_{12}$,OH |
| N,O,P1 | $C_{13}$,OH |
| P2 | $C_{10}$,OH |
| 3 | $C_9$ |
| D | $C_{10}$, olefin |
| Q | $C_{10}$,OH |
| R | $C_{10}$, branched, olefin |
| S | $C_{10}$, branched |
| B1 | $C_{10}$ |
| B2, B4, B5 | $C_{11}$, branched |
| B3 | $C_{11}$ |
| C1, C3 | $C_{12}$, branched |
| C2, C4 | $C_{12}$ |
| C5, C6 | $C_{13}$, branched |

The AAD-216 antiobiotics were analyzed by fast atom bombardment mass spectroscopy (FAB-MS). The molecular weights (M+H) of clusters of each factor are shown in the table which follows.

| Factor | MW (M + H) |
|---|---|
| F1,2,3 | 1817 |
| G,H,J,K,L | 1831 |
| M1 | 1815 |
| 2 | 1829 |
| 3 | 1845 |
| N,O | 1845 |
| P1 | 1845 |
| 2 | 1803 |
| 3 | 1773 |
| Q | 1803 |
| D | 1785 |
| R | 1785 |
| S | 1787 |
| B1 | 1771 |
| 2 | 1801 |
| B3, B4 | 1801 |
| B5 | 1785 |
| C1 | 1815 |
| C2 | 1815 |
| C3, C4 | 1799 |
| C5, C6 | 1829 |

The mannosyl pseudoaglycones ($R_2=H$) of the AAD-216 antibiotics have a molecular weight of 1457, except that the molecular weight of factors M2, M3, B1, B5, C3 and C4 is 1441, because these are desoxy analogs. The mannosyl pseudoaglycones of all of the factors, prepared by hydrolysis of the complex, migrated with the mannosyl pseudoaglycone of AAD-216 A, B and C in HPLC, except, of course, for the mannosyl pseudoaglycones of the desoxy analogs. For comparative purposes, the following table lists the GC-RT, the atomic masses (M+H) and the predicted empirical formulae of the fatty acids ($R_3COOH$) of AAD-216 A, B and C and the atomic masses by FAB-MS of AAD-216 A, B and C.

| Factor | MW (M + H) | GC R-T | MW | Formula ($R_1COOH$) |
|---|---|---|---|---|
| A | 1787 | 7.9 | 186 | $C_{10}$ |
| B | 1801 | 8.7 | 200 | $C_{11}$ (branched) |
| C | 1815 | 10.0 | 214 | $C_{12}$ (branched) |

The AAD-609 complex is produced upon fermentation of *K. aridum largum* (SK&F-AAD-609) or an active mutant or derivative thereof in an aqueous nutrient medium containing assimilable sources of nitrogen and carbon under submerged aerobic conditions. The complex comprises a mixture of the novel AAD-609 antibiotics, the major factors being designated A, B, C, $C_2$ and D, as well as certain AAD-216 antibiotics (AAD 216 A, B and C have been recovered. Typically, fermentation is carried out at 20° to 37° C. with aeration for 10 to 100 hours. By "active mutant or derivative thereof" is meant a mutant or derivative of SK&F-AAD-609 which is capable of producing one or more AAD-216 or AAD-609 antibiotics in recoverable quantity. Such mutants or derivatives can be prepared by standard techniques including irradiation, selection and chemical mutagenesis. AAD-609 producers can be readily selected by techniques illustrated herein.

Production of the AAD-609 antibiotics is greatest between 30 to 70 hours, with a gradual drift towards an increase in AAD-216 production. It appears that over time, the AAD-609 antibiotics are biologically converted to the AAD-216 antibiotics. This conclusion is supported by experiments in which AAD-609 compounds were incorporated into a culture of *K. aridum shearer* (SK&F-AAD-216) and were converted into AAD-216 antibiotics.

The AAD-609 complex can be recovered from the fermentation broth by clarifying the whole fermentation broth, such as by filtration or centrifugation. The complex can be isolated by direct application of the clarified fermentation broth (pH 7) to a non-functional resin. The complex has an isoelectric point of 5.2. An XAD-7 methanol eluate can then be purified to yield AAD-609 complex by HPLC (e.g., reverse phase) or by affinity chromatography such as on an Affigel ® 10-D-ala-D-ala support (N-hydroxy succinamide esters of a crosslinked agarose gel bead support having a neutral 10 carbon atom spacer) or other solid matrix. Alternatively, the crude, clarified fermentation broth can be applied directly to the affinity support.

HPLC analysis of clarified broths and cell extracts (See, Examples 3 and 4, below) showed that both sources contained glycopeptide antibiotics. Identification by co-injection with authentic AAD-216 standards determined that the cell extract contained mostly the novel AAD-609 components, whereas, the broth was a source of both these components and the AAD-216 complex. These results are in agreement with previous observations showing that the clarified broth from *Kibdelosporangium aridum* (AAD-216) was the major source of the AAD-216 complex. Although small-scale experiments revealed that pure preparations of the AAD-609 antibiotics can be prepared in a one-step affinity isolation procedure from clarified broth, a preliminary chromatography step on XAD-7 was added to preserve the life-time of the affinity support by removing impurities which tend to precipitate in the concentrated broth upon storage, prior to the affinity step.

Prior studies determined that elution of affinity-bound glycopeptides is highly dependent on their physical properties, mainly hydrophobicity and isoelectric point. Because of their unusually low isoelectric point (3.8), the AAD-216 antibiotics are eluted with combinations of acetonitrile and $H_2O$, whereas, vancomycin and ristocetin which have isoelectric points of 8.2 and 8.4 respectively require both high pH and an organic modifier for good product recovery. Based on these observations a unique differential elution procedure is used to separate the two types of affinity-bound complexes produced by AAD-609 from an Affigel 10-D-Ala-D-Ala support. Trial studies showed that the AAD-216 antibiotics were eluted with acetonitrile/$H_2O$ mixtures while maintaining binding of the AAD-609 components. These were eluted under conditions used for vancomycin. Preliminary studies in our laboratory indicated that the behavior and recovery of all components in each complex were similar. Therefore, the yields of AAD-216 A and AAD-609 A are representative of the yields of their respective complexes.

The individual factors of the AAD-609 complex, can be resolved by HPLC, if desired. The AAD-609 antibiotics correspond to the AAD-216 antibiotics. Four of these have been isolated and characterized. All were shown to be substituted by mannose at the free hydroxyl in the D ring and by a glycolipid (N-acyl-glucosamine) at the free hydroxyl in the B ring.

Factors A, B, C, $C_2$ and D exhibited the following retention times (RT) in analytical HPLC under differing conditions (I, II and III)*.

*HPLC Conditions

| Factor | HPLC-RT | | |
|---|---|---|---|
| | I | II | III |
| A | 15.0 | 14.6 | 6.75 |
| B | 15.8 | 15.6 | 9.18 |
| C | 16.7 | 16.4 | 11.75 |
| $C_2$ | | | 12.14 |
| D | 15.0 | 14.6 | 4.94 |

In all cases, the column was an Ultrasphere ODS, 5 micron (4.6×150 mm) (Beckman Instruments, Fullerton, California), the flow rate was 1.5 ml/min and detection was by UV absorbance at 220 nm. Gradients were as follows:

I. 7-34% acetonitrile (7% for 1 minute, ramp to 34% over 13 minutes and hold at 34%) in buffer (0.1 M potassium phosphate (pH 3.2)).

II. 5.35% acetonitrile (5% for 1 minute, ramp to 35% over 13 minutes and hold at 35%) in buffer (0.025 M potassium phosphate (pH 6.0)).

III. 30-40% acetonitrile (30% for 1 minute, ramp to 40% over 10 minutes and hold at 40%) in buffer.

As evident from the HPLC retention times, the components A, B and C are similar to the AAD-216 antibiotics and teicoplanin. It is interesting to note that the order of elution of AAD-609 A, B, and C is prior to the corresponding AAD-216 A, B, and C at pH 3.2 and follow the AAD-216 antibiotics at pH 6.0. As previously observed during the purification, component AAD-609 C consists of two species. Under conditions III, the two are separable upon rechromatography on the reversed phase column.

Other physical properties of AAD-609 A, B, $CC_2$ and D are listed in the following table.

| | A | B | C-$C_2$ | D |
|---|---|---|---|---|
| Empirical formula | $C_{81}H_{84}$—$N_8O_{29}Cl_4$ | $C_{82}H_{86}$—$N_8O_{29}Cl_4$ | $C_{83}H_{88}$—$N_8O_{29}Cl_4$ | $C_{81}H_{82}$—$N_8O_{29}Cl_4$ |
| Molecular Weight (FAB-MS) | 1772 | 1786 | 1800 | 1770 |
| $\alpha_D^{20}$ (1%, $H_2O$) | −58 | −55 | −49 | −65 |
| $E_{1\ cm}^{1\%}$ values - | | | | |
| $\lambda_{max}$ = 280 nm, .1NHCl | 53 | 53 | 47 | 52 |
| $\lambda_{max}$ = 300 nm, .1NNaOH | 97 | 85 | 78 | 84 |
| Ignition residue (%) | 0.05 | 0 | 0.05 | 0.20 |
| TGA (%) | 8.2 | 6.7 | 8.1 | 7.9 |

All four components have identical UV spectra and exhibit a bathochromic shift from 280 nm, under neutral or acidic conditions, to 300 nm in base. The IR spectrum of AAD-609 A is representative of the group with significant absorbance frequencies observed at 3400, 2940, 1660, 1595, 1500, 1460, 1420, 1390, 1310, 1290, 1230, 1140, 1060, 1010, 810 and 730 cm$^{-1}$. All of the components are optically active.

The molecular weights of the AAD-609 glycopeptides shown above were determined by FAB-mass spectroscopy. Aside from the molecular ion, the most notable fragment in all four spectra occurs at 1458 mass unit. This is identical to the molecular weight of the pseduoaglycone of the AAD-216 antibiotics. Furthermore, following mild acid hydrolysis the complex is converted to a single HPLC component which has an identical retention time (co-injection) to an authentic standard of the AAD-216 pseudo aglycone ($R_2$=—H) The same observation was made when each pure glycopeptide was hydrolyzed individually.

The carbohydrate content is identical for all AAD-609 components and revealed that the antibiotics contain both mannose and an N-acyl-glucosamine moiety. AAD-609-D is the first reported major component of a glycopeptide antibiotic complex having an unsaturated fatty acid substituent.

Tabulated below are the pKa values obtained for AAD-609 components A, B, $CC_2$ and D. Previous results obtained on AAD-216 A are shown for comparison. As in the case of AAD-216 A, these samples were titrated in 30:70 acetonitrile:water; thus, the results are apparent values.

| AAD-216A (Averaged) | AAD-609A | AAD-609B | AAD-609$CC_2$ | AAD-609D | Assignment |
|---|---|---|---|---|---|
| 3.0 | 3.4 | 3.5 | 3.6 | 3.4 | (A) |
| 4.9 | — | — | — | — | (B) |
| 7.4 | 7.1 | 7.1 | 7.2 | 7.0 | (C) |
| 8.4 | 8.2 | 8.1 | 8.4 | 8.0 | (D) |
| 10.0 | 9.7 | 9.7 | 9.9 | 9.3 | (D) |
| 10.3 | 10.4 | 10.6 | 10.6 | 10.2 | (D) |
| (1) | 11.7 | (2) | 11.6 | 11.6 | (D) |

(A) carboxyl on aglycone
(B) carboxyl on side chain
(C) amino group on aglycone
(D) phenolic OH
(1) calculation limited to 6 pK values
(2) program was unable to fit data to a sixth pK The potentiometric titration identified seven titratable groups. Unlike AAD-216, the AAD-609 species do not contain the carboxyl group having a pKa value at 4.9. The absence of this carboxyl group is also expressed by the measured isoelectric point of 5.2 versus 3.8 for the AAD-216 factors. This value confirms the prediction of a higher isoelectric point made by the elution conditions of the affinity column. It is also the basis for the observed shift in HPLC retention times when the pH of the mobile phase is increased from 3.2 to 6.

$R_3$ in AAD-609 A, B, C, $C_2$ and D corresponds to $R_3$ in AAD-216 A, B, C, $C_2$ and D. Thus, in AAD-609 A, $R_3$ is $(CH_2)_8CH_3$; in AAD-609B, $R_3$ is $(CH_2)_7CH(CH_3)_2$; in AAD-609 D, $R_3$ is $C_9$ unsaturated alkyl; and in AAD-609 $C_2$, $R_3$ is $(CH_2)_{11}CH_3$.

The aglycone, the mannosyl pseudoaglycone ($R_2 = -H$) and the individual, or factor, pseudoaglycones ($R_1 = -H$) of the AAD-609 antibiotics are prepared as described in U.S. Pat. No. 4,521,335. The mannosyl pseudoglycone ($R_2 = -H$) and the aglycone ($R_1$ and $R_2 = -H$) of factors A, B, C and D are identical to the mannosyl pseudoaglycone and the aglycone, respectively, of AAD-216 A, B and C.

Each of the AAD-609 factors, as well as each of the AAD-216 factors, and the entire AAD-609 complex have antibaterial activity and increase propionate production in the rumen of ruminant animals and in the cecum of non-ruminant animals. Thus, the complex, any of its factors or any mixture of its factors can be used as antibacterial agents or as feed utilization efficiency enhancing agents.

In vitro minimum inhibitory concentrations (MIC) of the AAD-609 complex and of Factors A, B, $CC_2$ and D, using standard microtiter assay procedures, against a number of microorganisms are reported in Table A, which follows.

Representative $ED_{50}$ data are shown in Table B, which follows.

TABLE B

| | Activity of AAD 609 antibiotics in mouse protection tests[1] | | | | | | | | |
|---|---|---|---|---|---|---|---|---|---|
| | Strains | | | | | | | | |
| | S. aureus HH127 | | S. aureus[2] 2620 | | S. epidermidis 2479 | | S. epidermidis[2] 651 | | S. faecalis 34358 |
| Compound | MIC[3] | $ED_{50}$ | MIC | $ED_{50}$ | MIC | $ED_{50}$ | MIC | $ED_{50}$ | MIC | $ED_{50}$ |
| Vancomycin | 1.6 | 1.4 | 2 | 6.7 | 3.1 | 4.1 | 3.1 | 4.8 | 3.1 | 12.5 |
| AAD-216 A | 3.1 | 2.2 | 4 | 29 | 25 | 8.2 | 100 | 50 | 0.4 | 16 |
| AAD-609 A | 1.6 | 6.2 | 2 | 21.5 | 12.5 | 4.8 | 50 | 50 | 0.4 | 38 |
| AAD-609 B | 1.6 | 5.8 | 2 | 18 | 12.5 | 8.2 | 50 | 50 | 0.2 | 50 |
| AAD-609 C | 1.6 | 8.5 | 4 | 8.4 | 12.5 | 22 | 25 | 50 | 0.2 | 50 |
| AAD-609 D | 1.6 | 2.5 | 4 | 11.3 | 12.5 | 6.2 | 50 | 50 | 0.8 | 35 |

[1]Mice dosed 1 and 5 H post infection s.c.; $ED_{50}$, mg/kg.
[2]Methicillin resistant strains.
[3]MIC, μg/ml.

Table C which follows shows representative serum half-life and maximum serum concentration data on AAD-609 A.

TABLE C

| Pharmacokinetics of AAD-609 A in mice | | |
|---|---|---|
| | Maximum serum concentration (μg/ml) | Elimination half-life (mins) |
| Vancomycin | 30 | 20 |
| AAD-609 A | 90 | 116 |
| AAD-216 A | 121 | 226 |

These data demonstrate the antibacterial activity of the AAD-609 antibiotics against gram positive pathogenic bacteria and that the AAA-609 antibiotics have a longer serum half-life and higher maximum serum concentration than vancomycin.

Based on data such as is represented above, and based on data showing antibacterial activity for the minor components and the mannosyl pseudoaglycone, the aglycone and the factor pseudoaglycones of AAD-216, it is concluded that the remaining factors of AAD-609, as well as the mannosyl pseudoaglycone, the aglycone and the factor pseudoaglycones of AAD-609 similarly have antibacterial activity. The agylcone and the mannosyl pseudoaglycone are, of course, the same as those derived from the AAD-216 antibiotics.

The invention includes within its scope pharmaceutical compositions containing at least one of the AAD-

TABLE A

| | Antibacterial activity of AAD 609 antibiotics and comparative glycopeptides. | | | | | |
|---|---|---|---|---|---|---|
| | Compound MIC (μg/ml) | | | | | |
| Test | | AAD 216 | AAD 609 | | | |
| Strains | Vancomycin | A | A | B | C | D |
| Staphylococcus aureus HH127 | 1.6 | 3.1 | 1.6 | 1.6 | 1.6 | 1.6 |
| S. aureus 910* | 1.6 | 3.1 | 1.6 | 1.6 | 1.6 | 1.6 |
| S. aureus 209P | 0.8 | 0.8 | 0.4 | 0.8 | 0.8 | 0.8 |
| S. aureus 674 | 1.6 | 3.1 | 0.8 | 0.8 | 1.6 | 1.6 |
| S. aureus 675 | 3.1 | 12.5 | 6.3 | 6.3 | 6.3 | 6.3 |
| S. epidermidis 2479 | 3.1 | 25 | 12.5 | 12.5 | 12.5 | 12.5 |
| S. epidermidis 2683 | 3.1 | 50 | 24 | 25 | 25 | 25 |
| S. epidermidis 651* | 3.1 | 100 | 50 | 50 | 25 | 50 |
| S. epidermidis 2265 | 1.6 | 50 | 25 | 25 | 25 | 50 |
| Streptococcus faecalis 657 | 3.1 | 0.8 | 0.4 | 0.2 | 0.2 | 0.8 |
| S. faecalis 34358 | 3.1 | 0.4 | 0.4 | 0.2 | 0.2 | 0.8 |
| Escherichia coli 12140 | >100 | >100 | >100 | >100 | >100 | >100 |
| Salmonella gallinarum BC-595 | 100 | >100 | >100 | >100 | >100 | >100 |
| Clostridium difficile | 2 | 0.25 | 0.5 | 0.5 | 1 | 0.5 |

*Methicillin resistant strain 609 factors of the invention and a pharmaceutically acceptable carrier. The compositions may also contain other active antibacterial agents. The compositions may be made up in any pharmaceutical form appropriate for the route of administration in question. Such compositions are exemplified by solid compositions for oral administration, such as tablets, capsules, pills, powders and granules; liquid compositions for oral administration such as solutions, suspensions, syrups and elixirs; preparations for parenteral administration such as sterile solutions, suspensions or emulsions; and preparations for topical administration such as gels, creams, ointments or salves.

For use as an antibacterial agent, the compositions are administered so that the concentration of the active ingredient is greater than the minimum inhibitory concentration for the particular organism treated.

The AAD-609 antibiotics were characterized in a rumen in vitro model to assess their potential as feed additives for ruminants. The effects on rumen fermentation of selected levels of AAD-609 Complex (containing only insignificant quantities, <5%, of AAD-216 antibiotics) were evaluated and compared to AAD-216 Complex, AAD-216 A, AAD-216 B, AAD-216 C, monensin, salinomycin and avoparcin. Specifically, strained rumen fluid (10 ml) obtained from a fistulated steer receiving a roughage ration, was mixed with 10 ml of nutrient broth (20 mg casein hydrolysate, 100 mg maltose, 15 mg urea, 400 mg solka floc (cellulose), 100 mg cellobiose and 100 mg starch) and with a selected growth promotant and incubated at 39° C., with oscillation, for 24 hours. Results, amounts of digestion products as a percentage of a control rumen fluid, are reported for acetate (ACE), propionate (PRO), isobutyrate (IBU), butyrate (BUT), isovalerate (IVA), total volatile fatty acids (TOTAL), ammonia nitrogen (AMO), lysine (LYS), percent propionate (% PR) and alpha amino nitrogen (AAN). Measurement of AMO, LYS and AAN was done with a sample taken from the incubation flask after 6 hours.

These results indicate that AAD-609 antibiotics increase propionate production in the rumen and, therefore, can be used to improve efficiency of feed utilization, to promote growth and to prevent and to treat ketosis. These results also indicate that AAD-609 antibiotics increase propionate production without significantly decreasing acetate and butyrate production. Therefore, these compounds can be used to improve milk production (increased fat-corrected milk yield) in lactating ruminants.

A swine in vitro model was used to characterize AAD-609 antibiotics as potential feed additives in swine and poultry. Mixed intestinal microflora were obtained from ileally-cannulated pigs. Virginiamycin, carbadox, AAD-216 and its components, and AAD-609 Complex (containing less than 5% AAD-216 antibiotics) were tested at one level. The response to AAD-609 was similar both qualitatively and quantitatively to AAD-216. Glucose (GLU) was spared from microbial degradation. Volatile fatty acids (TOTAL) were the major end-product of microbial metabolism while lactic acid production were reduced. It is known that AAD-216 is an effective growth promoter in the chick. Since AAD-609 and AAD-216 give similar in vitro results, it is expected that AAD-609 has similar growth-promoting activity in monogastric animals. Also, the in vitro activity of AAD-609 is similar to the activity previously observed with bacitracin in this model. Bacitracin is a known growth promoter in pigs, supporting the concept of AAD-609 as a swine growth promoter.

The swine in vitro model was carried out by incubating 1.5 ml of cecum fluid, from a swine fed normal rations, mixed with 1.5 ml of a nutrient broth (3 mg casein hydrolysate, 30 mg maltose, 1.25 mg urea, 0.5 mg lysine, and 30 mg cellobiose) and with up to 166.67 parts per million of a selected growth promotant at 39° C., with oscillation, for about 4–5 hours. Results, percentage of control, are reported in the following table in which all abbreviations are as above except that LLA means L-lactate and ETOH means ethanol.

| Factor | PPM | ETOH | ACE | PRO | IBU | BUT | IVA | VAL | TOTAL | % PR | AMO | LYS | AAN |
|---|---|---|---|---|---|---|---|---|---|---|---|---|---|
| AAD-216 | 50.00 | 0 | 97 | 146 | 102 | 96 | 105 | 37 | 105 | 139 | 107 | 120 | 214 |
|  | 5.00 | 0 | 98 | 147 | 89 | 82 | 59 | 60 | 101 | 147 | 92 | 132 | 171 |
|  | 0.50 | 0 | 99 | 108 | 115 | 95 | 105 | 101 | 100 | 108 | 93 | 168 | 126 |
| AAD-216 A | 50.00 | 0 | 93 | 138 | 112 | 87 | 98 | 26 | 98 | 140 | 109 | 168 | 195 |
|  | 5.00 | 0 | 105 | 153 | 75 | 81 | 48 | 56 | 103 | 148 | 101 | 144 | 153 |
|  | 0.50 | 0 | 96 | 107 | 125 | 100 | 124 | 105 | 101 | 106 | 102 | 108 | 76 |
| AAD-216 B | 50.00 | 0 | 103 | 159 | 123 | 98 | 111 | 28 | 110 | 144 | 107 | 132 | 178 |
|  | 5.00 | 0 | 106 | 153 | 95 | 88 | 67 | 86 | 108 | 141 | 93 | 120 | 140 |
|  | 0.50 | 0 | 107 | 108 | 108 | 97 | 94 | 101 | 103 | 104 | 96 | 96 | 121 |
| AAD-216 C | 50.00 | 0 | 98 | 154 | 111 | 88 | 87 | 30 | 104 | 149 | 106 | 144 | 166 |
|  | 5.00 | 0 | 96 | 148 | 86 | 83 | 56 | 51 | 100 | 148 | 98 | 102 | 136 |
|  | 0.50 | 0 | 94 | 105 | 123 | 101 | 123 | 102 | 100 | 105 | 99 | 78 | 96 |
| Monensin | 50.00 | 0 | 96 | 258 | 123 | 53 | 132 | 81 | 117 | 221 | 101 | 186 | 248 |
|  | 5.00 | 0 | 101 | 208 | 84 | 61 | 103 | 92 | 110 | 189 | 101 | 144 | 185 |
|  | 0.50 | 0 | 100 | 141 | 112 | 92 | 150 | 100 | 108 | 131 | 103 | 78 | 117 |
| Salinomycin | 50.00 | 0 | 98 | 289 | 111 | 54 | 146 | 96 | 126 | 230 | 118 | 180 | 258 |
|  | 5.00 | 0 | 91 | 200 | 107 | 59 | 98 | 74 | 104 | 193 | 99 | 102 | 204 |
|  | 0.50 | 0 | 109 | 164 | 90 | 84 | 116 | 90 | 112 | 147 | 101 | 24 | 131 |
| Avoparcin | 50.00 | 0 | 98 | 130 | 117 | 90 | 90 | 68 | 101 | 129 | 111 | 114 | 182 |
|  | 5.00 | 0 | 94 | 116 | 103 | 82 | 94 | 73 | 94 | 123 | 97 | 150 | 120 |
|  | 0.50 | 0 | 100 | 104 | 91 | 103 | 97 | 103 | 102 | 102 | 93 | 120 | 99 |
| AAD-609 | 50.00 | 0 | 98 | 151 | 142 | 101 | 128 | 42 | 109 | 138 | 115 | 138 | 161 |
|  | 25.00 | 0 | 99 | 151 | 90 | 89 | 69 | 37 | 103 | 146 | 104 | 126 | 166 |
|  | 5.00 | 0 | 103 | 159 | 97 | 86 | 64 | 62 | 106 | 149 | 98 | 132 | 208 |
|  | 0.50 | 0 | 100 | 111 | 121 | 101 | 118 | 106 | 103 | 107 | 98 | 90 | 96 |

| Factor | ETOH | ACE | PRO | IBU | BUT | IVA | VAL | TOTAL | % PR | LYS | GLU | LLA |
|---|---|---|---|---|---|---|---|---|---|---|---|---|
| Virginiamycin | 25 | 53 | 44 | 0 | 153 | 0 | 0 | 63 | 69 | 94 | 180 | 4 |
| Carbadox | 62 | 47 | 11 | 0 | 46 | 0 | 0 | 30 | 38 | 79 | 138 | 9 |
| AAD-216 | 159 | 238 | 319 | 0 | 160 | 0 | 0 | 274 | 116 | 44 | 180 | 2 |
| AAD-216 A | 167 | 200 | 276 | 0 | 147 | 0 | 0 | 236 | 117 | 35 | 180 | 2 |
| AAD-216 B | 104 | 217 | 305 | 0 | 154 | 0 | 0 | 257 | 119 | 25 | 180 | 2 |
| AAD-216 C | 0 | 175 | 281 | 0 | 105 | 0 | 0 | 221 | 127 | 29 | 181 | 2 |
| AAD-609 | 0 | 235 | 301 | 0 | 164 | 0 | 0 | 265 | 114 | 20 | 181 | 2 |

The effects of virginiamycin, AAD-609 Complex (containing less than 5% AAD-216 antibiotics) and AAD-216 Complex on growth of chicks were evaluated as follows. Hubbard cross day-old chicks were housed in wire-floored poultry caging. Eight chicks were included in each pen/rep. Weights and feed intakes were recorded on days 10 and 17. Results showing animal weight as a percentage of a control fed a normal rye-based ration and animal feed intake per unit weight gain as a percentage of animal feed intake (g) per unit weight gain (g) of the controls are reported in the following table.

| FACTOR | DOSE PPM | # OF REPS | DAY 10 | DAY 17 | 3-10 | 10-17 | 3-17 | MORTAL-ITY |
|---|---|---|---|---|---|---|---|---|
| | | | WEIGHT | | FEED/GAIN | | | |
| Virginiamycin | 50.0 | 8 | 101.5 | 120.2 | 92.8 | 74.3 | 83.2 | 2 |
| AAD-609 | 10.0 | 8 | 102.2 | 113.0 | 95.6 | 83.8 | 89.3 | 3 |
| Virginiamycin | 10.0 | 8 | 100.3 | 101.8 | 99.8 | 96.6 | 97.5 | 4 |
| AAD-216 | 10.0 | 8 | 102.9 | 118.9 | 94.6 | 80.4 | 87.8 | 1 |
| | | | GRAMS | | GRAMS/GRAM | | | |
| Control | 0.0 | 8 | 174.9 | 300.8 | 1.502 | 2.577 | 2.049 | 0 |

The above results indicate that the AAD-609 antibiotics are effective in improving the feed utilization efficiency as evidenced by increased weight gain in treated animals.

The feed compositions of this invention comprise the normal feed rations of the meat and milk producing animals supplemented by a quantity of an active ingredient selected from one or more of the AAD-609 factors of the invention which is effective for improving the feed efficiency of the animals but which is not toxic or noxious to a degree that the animals will reduce ingestion of the ration. The quantity of the active ingredient will vary, as is known to the art, with factors such as the cost of the ingredient, the species and the size of the animals, the relative activity of the compound of formula I and the type of feed ration used as the basal feed. The quantity of the active ingredient to increase propionate, to improve feed utilization efficiency, to promote growth and to treat or prevent ketosis should be an amount which increases propionate levels in the rumen or cecum and, to improve milk production, the quantity should be an amount which increases propionate level in the rumen but which does not significantly decrease acetate and butyrate levels. Such quantities are readily determined by standard techniques. See, for example, Scheifinger, U.S. Pat. No. 4,430,328 and Smith et al., GB No.-2,137,087-A, with respect to milk production.

Representative feed rations for swine and poultry are as follows:

A swine ration for growing hogs of 40-100 pounds body weight is prepared using the following formula:

| Corn, ground | 78.15% |
|---|---|
| Soybean oil meal, 44% | 17.0% |

| -continued | |
|---|---|
| Meat scraps, 50% | 3.0% |
| Oyster shell flavor | 0.4% |
| Bone meal | 0.5% |
| Zinc oxide | 0.01% |
| Vitamin A, B, B$_{12}$ & D | optional |

A chicken ration for broilers is prepared using the following formula:

| Yellow corn meal | 67.35% |
|---|---|
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin B$_{12}$ | 0.10% |
| Manganese sulfate | 0.02% |
| Vitamin mix | 0.06% |

Swine feed from weanling to fattening or finishing rations may be supplemented. Swine eat from about 2 lb. of ration per day (for a 25 lb. pig) to 9 lb. per day (for a 150 lb. pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal or soybean meal. The broiler rations, often, contain high energy supplements such as added fats, proteins and vitamins. Turkey rations are similar, but comprise only a starting ration and a growing ration. Chickens or pheasants eat from .03-0.3 lbs. of feed per day, turkeys twice that much. Estimated intake of feed is dependent on the weight and age of the meat producing animal.

The active ingredients selected from the AAD-609 antibiotics or a mixture thereof are mixed uniformly with such feed rations to give supplemented rations which are, then fed as to custom, which is, most often, ad libitum. Conveniently, to do this, a premix of the supplemental growth promotant of this invention, optionally combined with or without other supplements known to this art such as an anthelmintic, a nitrogen source or an antibiotic, for example, virginiamycin or oxytetracycline is prepared by the manufacturer for sale to the formulators or feed lot operators. The concentration of the active ingredients in the premix is usually from 5–75% by weight or a concentration 100–2000 times greater than that in the complete feed ration. The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ration which is fed to the target animal. Such premix compositions are included in the term "feed compositions" as used herein.

The concentration of the active ingredients in the complete ration is a nontoxic but active quantity chosen, for example, from a range of about 1–1000 parts of active ingredient by weight per million parts of whole feed (ppm) or about 2–115 grams per ton. Advantageously, a nontoxic quantity of active ingredient is chosen from the range of 10–50 ppm.

This method of the invention comprises feeding to monogastric or ruminant, meat or milk producing animals, especially beef and dairy cattle, sheep, swine and poultry, an effective growth promoting but nontoxic quantity of an AAD-609 antibiotic. Other monogastric animals whose digestive tract also features fermentation in a cecum or cecum-like chamber also features fermentation.

The supplemented feed rations, described above, are presented to the animal by methods known to the art. Ad libitum feeding in the pasture, pen or growing shed is most convenient to increase the growth and milking rate of the animal and to increase the feed efficiency of the operation.

The following examples are illustrative of the production, isolation and purification of the antibiotics of the present invention and are not therefore to be considered as limiting the present invention described in the claims appended hereto.

EXAMPLES

EXAMPLE 1

Fermentation of *K. aridum largum*, SK&F-AAD-609

An agar slant culture of SK&F AAD-609 was grown at 8° C. for 14 days. The slant contents were dispersed and suspended in 10 ml of sterile distilled water and inoculated into 500 ml of seed medium 13H contained in a 4L aspirator bottle. This seed culture was incubated at 28° C. for 4 days on a reciprocal shaker at 250 rpm and 5 cm throw. The entire seed was transferred to 9.5 liters of medium 13H in a 14 liter New Brunswick Fermentor (M-19). The fermentor was controlled at 26° C. for 3 days with agitation at 400 rpm and aeration at 4 liters/min. The final seed was prepared by transferring 10 liters of the culture to 50 liters of medium 13H in a 75 liter Chemapac fermentor. This was controlled at 26° C. for 3 days, with agitation at 250 rpm and aeration at 25 liters/min. This was used to inoculate 500 liters of production medium V-2 in a 750 liter ABEC fermentor. The production stage was maintained at 28° C. with agitation at 150 rpm and aeration at 200 liters/min. The production of the AAD-609 complex was monitored carefully, by analytical HPLC, and the products were harvested at 45 hours by which time the AAD-609 antibiotics were the predominant components. Subsequent to this point the production of AAD-216 antibiotics markedly surpassed the AAD-609 antibiotics by a factor of 40:1. The early harvest facilitated isolation of the novel compounds from the known components. Medium 13H is composed of the following ingredients: distilled water (1), starch (15 g), sucrose (5 g), dextrose, (5 g), soy peptone (7.5 g), corn steep liquor (5 g), $K_2HPO_4$ (1.5 g), NaCl (0.5), $CaCO_3$ (1.5 g), mineral supplement (5 ml) of $ZnSO_4 \cdot 7H_2O$ (2.8 g/l), Ammonium ferric citrate (2.7 g/l), $CuSO_4 \cdot 5H_2O$ (0.125 g/l), $MnSO_4 \cdot H_2O$ (1 g/l), $CoCl_2 \cdot 6H_2O \cdot 6H_2O$ (Q.1 g/l), $Na_2B_4O_7 \cdot 10H_2O$ (0.1 g/l), $Na_2MoO_4 \cdot 2H_2O$ (0.05 g/l).

Medium V-2 is composed of the following ingredients: distilled water (1 l) soybean meal (15 g), beet molasses (10 g), Estransan-4 (10 g), glucose or glycerol (10 g) and NaCl (0.3 g).

EXAMPLE 2

Dicrimination of Novel Components

A 250 ml fermentation culture of SK&F-AAD-609, prepared substantially as described in Example 1, above, was clarified by centrifugation and 100 ml of filtrate was lyophilized to yield 2.0 g which was stored at 4° C. The dried material was then reconstituted to 20 ml with 0.02 M sodium phosphate buffer (pH 7). Insoluble material was removed by centrifugation at 2000×g for 10 min at 4° C.

The concentration of antibiotics in the supernatant was too low to be accurately identified and measured by HPLC analysis.

The supernatant was batched onto 2 ml of Affigel 10-D-ala-D-ala (capacity=3 mg/ml) (Bio-Rad Laboratories, Richmond, California) for 30 min and then transferred to a 15 mm diameter column. The gel was washed sequentially with 20 ml each of 0.02 M sodium phosphate buffer (pH 7), 0.5 M triethylammonium bicarbonate (pH 9) containing 30% acetonitrile and, finally, 0.1 M ammonium hydroxide containing 70% acetonitrile. Fractions were monitored by absorbance and activity against *Bacillus subtilis*. The majority of *B. subtilis* active material eluted with the 70% acetonitrile solution. Active fractions were pooled, lyophilized and reconstituted into 1.5 ml of 0.02 M sodium phosphate buffer (pH 7) and assayed by HPLC using a Beckman Ultrasphere ODS, 4.6×150 mm; eluted with 25–40% acetonitrile in 0.1 M sodium phosphate (pH 3.2); flow rate of 2 ml min; monitored by absorbance at 254 nm.

The HPLC analysis showed presence of three components which co-eluted with AAD-216 A, B and C standards as well as other novel components, including AAD-609 A, B and C which were the major components and which had the retention times shown in Table Ex. 2, below. The total yield of glycopeptide antibiotics was approximately 0.3 mg, with an overall concentration from the starting broth of about 65-fold.

TABLE Ex. 2

| Glycopeptide | AAD-216 Standard | | AAD-609 Isolate | | Co-injection of 1:1 mixture | |
|---|---|---|---|---|---|---|
| | RT | Area | RT | Area | RT | Area |
| AAD-609 A | 6.86 | 113680 | 6.46 | 184680 | 6.45 | 71213 |
| AAD-216 A | | | 6.84 | 84327 | 6.84 | 116500 |
| AAD-609 B | 7.59 | 169970 | 7.21 | 338820 | 7.21 | 153780 |
| AAD-216 B | | | 7.53 | 39718 | 7.53 | 142780 |
| AAD-609 C | 8.45 | 130120 | 8.07 | 342500 | 8.07 | 115430 |
| AAD-216 C | | | | | 8.38 | 76637 |

These results demonstrate that affinity isolation in combination with HPLC is a rapid and efficient screening technique for novel glycopeptide antibiotics. This technique allows for simple discrimination of glycopeptide antibiotic producers without a need for initial concentration of a broth culture, extensive purification, or large-scale fermentation.

EXAMPLE 3

Isolation of AAD-609 Complex from Broth

A fermentation broth, 600 L, prepared substantially as described in Example 1, above, was clarified by rotary drum filtration. Following clarification, samples of the broth (430 L) were pretreated in the following manner: a fresh $C_{18}$ Sep-Pak cartridge (Waters Associates) was first sequentially washed with 4 ml each of $CH_3CN$, $H_2O$, and 0.1 M pH 3.2 phosphate. A 1.0 ml broth aliquot previously adjusted to pH 6.0–6.5 with dilute $H_3PO_4$ was passed through the cartridge. The cartridge was then sequentially eluted with 2.0 ml each of the following: 0.1 M pH 3.2 phosphate, 20% $CH_3CN/0.1$ M, pH 3.2, phosphate, and 50% $CH_3CN/0.1$ M pH 3.2 phosphate. The 50% eluate was collected in a vial, and a 25 $\mu$l aliquot was taken for HPLC assay. Acetonitrile used was glass distilled HPLC grade (Burdick and Jackson Laboratories, Muskegon, Michigan); water used was HPLC grade produced from an in-house Milli-Q system. Phosphate solutions were prepared by addition of solid KOH to 0.1 M $H_3PO_4$, both of which were ACS reagent grade.

The clarified broth (not pretreated) was adjusted to pH 7 with 2 N HCl and directly applied to Amberlite XAD-7 (Rohm and Haas, Philadelphia, Pa.). After washing with water, the AAD-609 Complex was recovered by elution with 60% (v/v) acetonitrile in water. The resulting eluate, 64 L, was concentrated to 4.5 L in a rising film evaporator and guantitated by analytical HPLC.

The concentrated XAD-7 eluate (4.5 L) was adjusted to pH 7 with 2N HCl and filtered through Whatman number 1 filter paper using precoat filter aid. The filtrate was combined with 600 ml Affi-gel 10-D-Ala-D-Ala (capacity=12 mg/ml) for 30 min in a batch-type procedure. The slurry was poured into a 4.5×60 cm glass column fitted with a filter disk and stopcock, and the spent was collected. The affinity gel was washed with 6 L of 0.02 M sodium phosphate at pH 7 followed by 3 L of 0.5 M NH$_4$OAc at pH 7.8. The AAD-216 complex was specifically eluted using a step-wise series of 3, 5, and 10% acetonitrile/H$_2$O washes (3, 2, 1 L) followed by elution of the AAD-609 components with 50% acetonitrile in 0.1 M NH$_4$OH. Fractions were collected in bulk volumes from 200–1000 ml and assayed by HPLC. Fractions containing the AAD-609 antibiotics were pooled and lyophilized to dryness. Following column regeneration with 2L of 30% acetonitrile in 0.4 M NaHCO$_3$ (pH 9.5), the spent material was recycled.

After initial washings with phosphate and acetate buffers to remove non-specifically bound contaminants the step-wise increment in acetonitrile of 3, 5 and 10% effectively eluted the bound AAD-216 antibiotics with less than 10% loss of the AAD-609 antibiotics. The AAD-216 fractions were discarded. The AAD-609 fractions were eluted in less than 2 columns volumes using 50% acetonitrile in 0.1 M NH$_4$OH with high recovery and no detectable contamination by the AAD-216 components.

A basic high performance liquid chromatograph (HPLC) consisting of two model 110A pumps and a model 420 gradient controller was used to quantitate the glycopeptide components of the broth by analytical HPLC. The UV detector was a Kratos SF770 Spectroflow Monitor with the wavelength set to 220 nm at a sensitivity of 0.04 AUFS. The system also included a Hewlett-Packard 3390A integrator and a Perkin-Elmer ISS-100 autosampler. The column (Beckman Ultrasphere $5 \times 10^{-6}$ M ODS 4.6 mm $\times$ 15 cm) was operated at a constant flow rate of 1.5 ml/min with a back pressure of 2000 PSIG (13.8 MPa). A mobile phase gradient was utilized, starting isocratically at 30:70 $CH_3CN$ - 0.1 M potassium phosphate (pH 3.2). After one minute, the gradient was started and the organic phase allowed to linearly increase to a final composition of 40:60 $CH_3CN$-phosphate over a ten minute interval. At the end of each run the column was re-equilibrated to the initial conditions. Quantitation was achieved by comparing the peak height of each novel glycopeptide to the peak height obtained for the corresponding AAD-216 analog at 5 $\mu$g/ml.

Table Ex. 3, which follows, reports the amounts of glycopeptide antibiotics (by analytical HPLC) present in the clarified broth (430 L) in the XAD-7 concentrated eluate (4.5 L) and in the pooled 50% acetonitrile fractions.

TABLE

Ex. 3

| Component | | Clarified Extract 430 L (mg) | XAD-7 Eulate 4.5 L (mg) | Affi-gel 10-D-Ala-D-Ala (mg) |
|---|---|---|---|---|
| AAD-609 | D | 903 | 1691 | 1879 |
| | A | 1462 | 1610 | 1885 |
| | B | 473 | 778 | 1155 |
| | C | 516 | 1013 | 887 |
| AAD-216 | A | 473 | — | — |
| | B | 344 | — | — |
| | C | 430 | — | — |

The yields of antibiotics prior to affinity chromatography show some variation due to the required Sep-Pak pretreatment of the less pure extracts.

EXAMPLE 4

Isolation of AAD-609 Factors from Cell Extracts

The cells obtained from clarification of the broth in Example 2, above, were extracted with 80 L of methanol at room temperature. Samples were pretreated as described in Example 3 and assayed by analytical HPLC. The extract (not pretreated) was concentrated to 20 L at 32° C. in a rising film evaporator and further concentrated to 8.25 L by rotary evaporation. The concentrated cell extracts was centrifuged at 4° C. for 60 min at 3000×g. After storage, at 4° C. for 2 weeks, the supernatant (7 L) was filtered through Whatman number 1 filter paper. The precipitate was washed with 1 L of distilled water and then with 2.5 L of 50% acetonitrile/water. After each wash desorbed, antibiotic was recovered by filtration through Whatman number 1 filter paper using precoat filter aid (Hyflo Super cel, Johns-Manville Products Corporation).

Glycopeptide products were purified from the 7 liters of methanol cell extract as described in Example 3, above, with the exception that the affinity gel was washed with 6 L of 10% methanol/water prior to product elution with 50% acetonitrile in 0.1 M NH$_4$OH.

The following table, Table Ex. 4, shows the retention times and approximate amounts recovered of AAD-609

A, B, CC$_2$ and D by analytical HPLC performed substantially as described in Example 3, above.

TABLE

| Component | | Ex. 4 Methanol Cell Extract[2] 80 L (mg) | Methanol Concentrate 8.25 L (mg) | Affinity (mg) |
|---|---|---|---|---|
| AAD-609 | D | 592 | 473 | 447 |
| | A | 1464 | 788 | 773 |
| | B | 1496 | 576 | 603 |
| | C | 2936 | 1739 | 984 |
| AAD-216 | A | 216 | — | — |
| | B | 80 | — | — |
| | C | 264 | — | — |

EXAMPLE 5

Preparative HPLC

To confirm the structural identity of the AAD-216 components produced by SKF-AAD-609, a fermentation broth not optimized for AAD-609 production was employed. The individual components of the AAD-216 complex were resolved using a 22 mm×300 mm prepacked Whatman Magnum-20 10 micron Partisil ODS-3 column equipped with a Beckman 112 preparative pump and ISCO V$_4$ variable wavelength detector. The chromatography was performed at a flow rate of 10–15 ml/min while monitoring the eluate at approximately 300 nm and collecting 25 ml fractions. The sample load was approximately 200 mg dissolved in 15% acetonitrile/0.1 M phosphate (pH 6). The components were eluted with an acetonitrite step gradient (28-30-32%).

AAD-609 components, purified substantially as described in Example 3, were purified as described above except that the sample load on the preparative reverse-phase column was increased to 1.0–1.5 g per injection, the step-wise gradient was extended to 26-28-30-32% and only the center portions of each of the resolved components were collected for physicochemical and structural elucidation analyses. After desalting and lyophilization, the yield of purified components from 4.38 g of affinity-purified complex were D:560 mg; A:550 mg; B:317 mg; and C:315 mg. All are fluffy white powders decomposing above 320° C. The side fractions contained additional amounts of AAD-609 antibiotics but were not recycled.

EXAMPLE 6

Mannosyl Pseudoaglycone

The glycolipid fragment was removed to prepare pseudoaglycone (R$_2$=—H) by mild acid the mannosyl hydrolysis in which solid samples of AAD-216 A, AAD-609 complex or individual AAD-609 Factors were dissolved in 0.1 M sodium phosphate, pH 3.2 at a concentration of 0.2 mg/ml and heated to 100° C. for 15 hr. in a sealed vacuum hydrolysis tube. The AAD-609 hydrolysis product was identified by the HPLC assay described above using co-injection with the authentic pseudoaglycone of AAD-216 as the standard.

EXAMPLE 7

Factor Pseudoaglycones

The Factor Pseudoaglycones (R$_1$=H) of AAD-609 A, B and C are prepared by treating each Factor, separately, in dimethylsulfoxide at 100° C. for 15 minutes and isolating the pseudoaglycone by reverse phase HPLC, substantially as described by Chan et al., U.S. Pat. No. 4,521,335.

The above disclosure fully describes the invention and preferred embodiments thereof. However, the invention is not limited to embodiments specifically described but rather includes all modifications coming within the scope of the following claims.

We claim:

1. A biologically pure culture of *Kibdelosporangium aridum largum* which has the identifying characteristics of ATCC 39922 and mutants and derivatives thereof, said microorganism and mutants and derivatives being capable of producing AAD-609 antibiotics of formula (I)

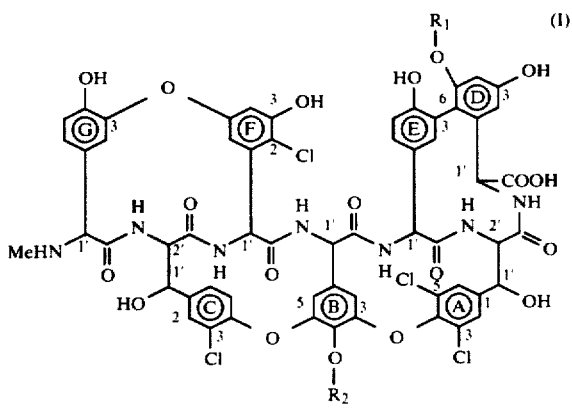

wherein R$_1$ is mannosyl or hydrogen, and R$_2$ is a glycolipid radical having the structure

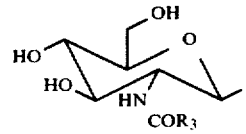

wherein R$_3$ is a C$_{8-12}$ alkyl or alkenyl, branched or linear, optionally substituted by hydroxyl, or the desoxy analog thereof in recoverable quantity upon cultivation in an aqueous nutrient medium containing assimilable sources of carbon and nitrogen.

2. An antibiotic complex isolated from a culture of *Kibdelosporangium aridum largum* which has the identifying characteristics of ATCC 39922 or an active mutant or derivative thereof which complex comprises AAD609 antibiotic compounds of claim 1.

3. An AAD-609 antibiotic which has the formula

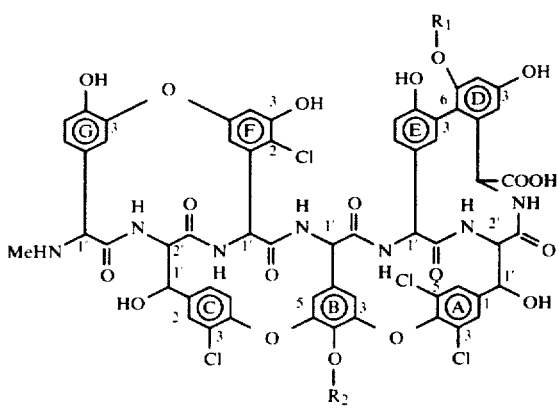

wherein $R_1$ is mannosyl or hydrogen, and $R_2$ is a glycolipid radical having the structure

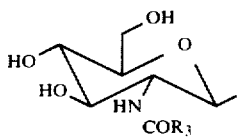

wherein $R_3$ is a $C_{8-12}$ alkyl or alkenyl, branched or linear, optionally substituted by hydroxyl, or the desoxy analog thereof.

4. The AAD-609 anitbiotic compound of claim 3 which is Factor A wherein $R_3$ is $-(CH_2)_8CH_3$.

5. The AAD-609 antibiotic compound of claim 3 which is Factor B wherein $R_3$ is $-(CH_2)_7CH(CH_3)_2$.

6. The AAD-609 antibiotic compound of claim 3 which is Factor C wherein $R_3$ is $-(CH_2)_8CH(CH_3)_2$.

7. The AAD-609 antibiotic compound of claim 3 which is Factor $C_2$ wherein $R_3$ is $-(CH_2)_{11}CH_3$.

8. The AAD-609 antibiotic compound of claim 3 which is Factor D wherein $R_3$ is $-(C_9H_{17}$.

9. A process for producing the antibiotic of claim 2 which comprises culturing *Kibdelosporangium aridum largum* ATCC 39922 or an active mutant or derivative thereof in an aerated aqueous nutrient medium containing an assimilable source of nitrogen and carbon under until a recoverable quantity of the complex is produced and isolating the complex therefrom.

10. The process of claim 9 which comprises isolating the complex by passing a fermentation broth or cell extract or both from the culture which has been clarified by filtration or centrifugation over a resin which does not contain functional groups and eluting the AAD-216 and AAD-609 antibiotics therefrom.

11. The process of claim 9 which further comprises separating the AAD-609 antibiotics from AAD-216 antibiotics present in the complex by affinity chromatography using eluents which separate them based on their hydrophobility and isoelectric points.

12. The process of claim 9 wherein the fermentation is carried out at 20° to 37° C. for 10 to 100 hours.

13. An antibacterial composition comprising an antibacterial effective amount of the antibiotic complex of claim 2 and a pharmaceutically acceptable carrier.

14. An antibacterial composition comprising an antibacterial effective amount of the antibiotic of claim 3 and a pharmaceutically acceptable carrier.

15. An antibacterial composition comprising an antibacterial effective amount of the antibiotic of claim 4 and a pharmaceutically acceptable carrier.

16. An antibacterial composition comprising an antibacterial effective amount of the antibiotic of claim 5 and a parmaceutically acceptable carrier.

17. An antibacterial composition comprising an antibacterial effective amount of the antibiotic of claim 6 and a pharmaceutically acceptable carrier.

18. An antibacterial composition comprising an antibacterial effective amount of the antibiotic of claim 7 and a pharmaceutically acceptable carrier.

19. An antibacterial composition comprising an antibacterial effective amount of the antibiotic of claim 8 and a pharmaceutically acceptable carrier.

20. A method for treating or preventing infection in an animal by a gram positive pathogenic bacteria which comprises orally, parenterally or topically administering to the animal the anitbacteraial composition of claim 13.

21. A method for treating or preventing infection in an animal by a gram positive pathogenic bacteria which comprises orally, parenterally or topically administering to the animal the antibacterial composition of claim 14.

22. A method for treating or preventing infection in an animal by a gram positive pathogenic bacteria which comprises orally, parenterally or topically administering to the animal the antibacterial composition of claim 15.

23. A method for treating or preventing infection in an animal by a gram positive pathogenic bacteria which comprises orally, parenterally or topically administering to the animal the antibacterial composition of claim 16.

24. A method for treating or preventing infection in an animal by a gram positive pathogenic bacteria which comprises orally, parenterally or topically administering to the animal the antibacterial composition of claim 17.

25. A method for treating or preventing infection in an animal by a gram positive pathogenic bacteria which comprises orally, parenterally or topically administering to the animal the antibacterial composition of claim 18.

26. A method for treating or preventing infection in an animal by a gram positive pathogenic bacteria which comprises orally, parenterally or topically administering to the animal the antibacterial composition of claim 19.

27. An animal feed composition comprising an animal feed supplemented by a non-toxic amount of the antibiotic complex of claim 2 which is effective in improving the feed utilization efficiency of a meat or milk producing animal.

28. An animal feed composition comprising an animal feed supplemented by a non-toxic amount of the antibiotic of claim 3 which is effective in improving the feed utilization efficiency of a meat or milk producing animal.

29. An animal feed composition comprising an animal feed supplemented by a non-toxic amount of the antibiotic of claim 4 which is effective in improving the feed utilization efficiency of a meat or milk producing animal.

30. An animal feed composition comprising an animal feed supplemented by a non-toxic amount of the antibiotic of claim 5 which is effective in improving the feed utilization efficiency of a meat or milk producing animal.

31. An animal feed composition comprising an animal feed supplemented by a non-toxic amount of the antibiotic of claim 6 which is effective in improving the feed utilization efficiency of a meat or milk producing animal.

32. An animal feed composition comprising an animal feed supplemented by a non-toxic amount of the antibiotic of claim 7 which is effective in improving the feed utilization efficiency of a meat or milk producing animal.

33. An animal feed composition comprising an animal feed supplemented by a non-toxic amount of the antibiotic of claim 8 which is effective in improving the feed utilization efficiency of a meat or milk producing animal.

34. An animal feed composition comprising an animal feed supplemented by a non-toxic amount of the antibiotic complex of claim 2 which is effective in increasing the propionate level in the rumen or cecum of a meat or milk producing animal.

35. An animal feed composition comprising an animal feed supplemented by a non-toxic amount of the antibiotic of claim 3 which is effective in increasing the propionate level in the rumen or cecum of a meat or milk producing animal.

36. An animal feed composition comprising an animal feed supplemented by a non-toxic amount of the antibiotic of claim 4 which is effective in increasing the propionate level in the rumen or cecum of a meat or milk producing animal.

37. An animal feed composition comprising an animal feed supplemented by a non-toxic amount of the antibiotic of claim 5 which is effective in increasing the propionate level in the rumen or cecum of a meat or milk producing animal.

38. An animal feed composition comprising an animal feed supplemented by a non-toxic amount of the antibiotic of claim 6 which is effective in increasing the propionate level in the rumen or cecum of a meat or milk producing animal 39. An animal feed composition comprising an animal feed supplemented by a non-toxic amount of the antibiotic of claim 7 which is effective in increasing the propionate level in the rumen or cecum of a meat or milk producing animal.

40. An animal feed composition comprising an animal feed supplemented by a non-toxic amount of the antibiotic of claim 8 which is effective in increasing the propionate level in the rumen or cecum of a meat or milk producing animal.

* * * * *

UNITED STATES PATENT OFFICE
CERTIFICATE OF CORRECTION

PATENT NO. : 4,694,069
DATED : September 15, 1987
INVENTOR(S) : John J. Dingerdissen, et al.

It is certified that error appears in the above-identified patent and that said Letters Patent are hereby corrected as shown below:

Column 21 - Example 6, line 52, before "pseudoaglycone" insert
-- the mannosyl -- .

line 52, after "acid" delete --"the mannosyl"

Signed and Sealed this

Twenty-first Day of June, 1988

Attest:

DONALD J. QUIGG

*Attesting Officer*  *Commissioner of Patents and Trademarks*